United States Patent
Gray, Jr. et al.

[11] Patent Number: 6,146,424
[45] Date of Patent: Nov. 14, 2000

[54] OFFSET PRESS-FIT TIBIAL STEM

[75] Inventors: Wayne P. Gray, Jr., Pflugerville, Tex.; Dennis L. Armstrong, Mesa, Ariz.

[73] Assignee: Sulzer Orthopedics Inc., Austin, Tex.

[21] Appl. No.: 09/126,361

[22] Filed: Jul. 30, 1998

[51] Int. Cl.[7] .................................................. A61F 2/38
[52] U.S. Cl. ................................... 623/20.34; 623/20.32; 623/20.15
[58] Field of Search .................. 623/20, 18, 23, 623/20.32, 20.33, 20.34, 20.15, 20.21

[56] References Cited

U.S. PATENT DOCUMENTS

| | | | |
|---|---|---|---|
| 4,268,920 | 5/1981 | Engelbrecht et al. | 623/20 |
| 4,759,767 | 7/1988 | Lacey | 623/20 |
| 5,133,760 | 7/1992 | Petersen et al. | 623/20 |
| 5,271,737 | 12/1993 | Baldwin et al. | 623/20 |
| 5,290,313 | 3/1994 | Heldreth | 623/20 |
| 5,593,449 | 1/1997 | Roberson, Jr. | 623/20 |
| 5,702,482 | 12/1997 | Thongpreda et al. | 623/23 |
| 5,782,920 | 7/1998 | Colleran | 623/18 |
| 5,944,756 | 8/1999 | Fischetti et al. | 623/18 |

*Primary Examiner*—David H. Willse
*Assistant Examiner*—Suzette J. Jackson
*Attorney, Agent, or Firm*—Philip S. Lyren; Kenneth S. Barrow

[57] ABSTRACT

An offset, press-fit tibial stem system includes a baseplate, a main body portion, a baseplate connection portion attached to the baseplate and being offset from, and connected to, the main body portion by a transition portion. The main body portion has a first centroidal axis passing therethrough and the baseplate connection portion has a second centroidal axis passing therethrough. The offset is such that the first centroidal axis and the second centroidal axis are slightly spaced apart and substantially parallel so as to each pass through the main body portion.

31 Claims, 4 Drawing Sheets

OFFSET PRESS-FIT TIBIAL STEM

BACKGROUND

The disclosures herein relate generally to knee implants and more particularly to a tibial stem including an offset which can be used to correct the tibial baseplate position medially or laterally.

Primary tibial implants often fail and must be replaced with a revision implant. An often encountered problem confronting a revision implant is bone loss and implant stability. The result of bone loss is that it precludes attaching a replacement implant directly to the proximal end of the tibia in the same manner as a primary implant by a fastening device or cement. Instead, the proximal end of the tibia is resected and a bore is formed using the intramedullary canal as a guide through the resected proximal end of the tibia to permit the placement of an implant stem. A baseplate is attached to the stem abutting the resected end of the tibia to receive and support an articulating surface.

The anatomy of the human tibia is variable. The tibia comprises an outer layer of hard cortical bone and an inner filling of relatively soft cancellous bone. The strength of the tibia is primarily derived from the cortical bone and should be preserved to support implants. Normally, the intermedullary canal is not in the actual center of the proximal tibia. As a result, when the bore is formed using the intramedullary canal, the stem which is placed in the bore may not be centered within the proximal tibia. Because the baseplate is mounted on the stem, the baseplate may not be ideally positioned with respect to the resected tibial surface. This can result in an overhang of the baseplate relative to the resected end of the tibia and a resulting irritation of soft surrounding tissue. The baseplate must therefore be kept within the confines of the tibia. As a result, it is often necessary to provide an offset, either medially or laterally, in order to properly orient the baseplate on the proximal tibia relative to the stem.

A surgeon may prefer to press-fit a tibial stem in the canal instead of cementing. In that case, the entire tibial canal is subsequently reamed out, i.e. all cancellous bone is removed. Subsequently, the surgeon trials with various size straight tibial stems having a baseplate attached, to find a stable press-fit with the cortical bone, but may find that the baseplate overhangs the proximal tibia. To correct for the overhang, the surgeon downsizes from the press-fit stem to a cemented stem in an effort to properly locate the baseplate, and then cements the implants in position.

If the bore is offset to compensate for the off-center canal within the tibia, the implant may be supported on some surface areas by the hard cortical bone and on other surface areas by the relatively softer cancellous bone. This is undesirable and may require a filler cement to stabilize and secure the stem. Also, if a subsequent replacement is required, the filler must be removed.

One attempt to overcome the above-mentioned problems with tibial stem implants is addressed in U.S. Pat. No. 5,133,760, which provides a universal modular prosthetic stem extension which may be installed on a prosthesis in a multiplicity of different orientations to compensate for a multiplicity of patient conditions. The stem includes a coupling mechanism allowing the stem to be rotated to any one of a multiplicity of rotative positions with respect to a prosthetic base so that the stem may be fixed in position relative to the base.

Another device is disclosed in U.S. Pat. No. 5,271,737 which comprises a combination baseplate fixed to an offset, straight tibial stem. The base includes an inferior surface for abutting a resected surface of the patient's tibia. The longitudinal center axis of the straight tibial stem extends from the inferior surface of the base and is offset from a center of the base. Interestingly, the offset places the stem in position to extend into the canal of the tibia so that it does not interfere with the cortical bone. As a result of the fixed arrangement, one baseplate and stem is required for a medial offset and another is required for a lateral offset.

A further device is disclosed in U.S. Pat. No. 5,290,313, which comprises a modular prosthesis system including a modular stem which has an attachment section for attachment to the base, a main body section for implanting into the canal in the tibia, and an angled transition section. The attachment section and main body section each include a respective longitudinal axis. These axes are parallel to each other and spaced apart to provide an offset therebetween. The offset is substantial, such that the axis of the attachment section intersects the transition section.

Therefor, what is needed is an offset tibial stem which can be press-fit distally so that only the baseplate requires cementing proximally, and so that the baseplate is offset either medially or laterally relative to the stem by an amount sufficient to center the baseplate on, and avoid overhanging of, the proximal tibial surface.

SUMMARY

One embodiment, accordingly, provides an offset, press-fit tibial system that allows a surgeon to interoperatively recenter the tibial baseplate on the proximal tibia of the patient, so that the main body of the tibial stem engages the inner cortical bone of the canal of a patient's tibia. To this end, an offset, press-fit implant stem comprises a main body portion of the stem, a baseplate connection portion of the stem, and a transition portion of the stem. The baseplate connection portion and the main body portion are interconnected by the transition portion. The baseplate connection portion is offset from the main body portion. The main body portion has a first centroidal axis passing therethrough, and the baseplate connection portion has a second centroidal axis passing therethrough. The offset is such that the first centroidal axis and the second centroidal axis each pass through the main body portion.

The principal advantage of this embodiment is that in a situation where a surgeon who prefers to press-fit a tibial stem rather than cementing, the surgeon can ream out the intermedullary canal until he can fill cortical bone with the stem. Then, instead of downsizing to prevent baseplate overhang, the distal end of the offset tibial stem can be press-fit into the canal so that the baseplate is centered on the proximal tibial surface without overhang.

DETAILED DESCRIPTION OF THE PREFERRED EMBODIMENT

Figure 1:
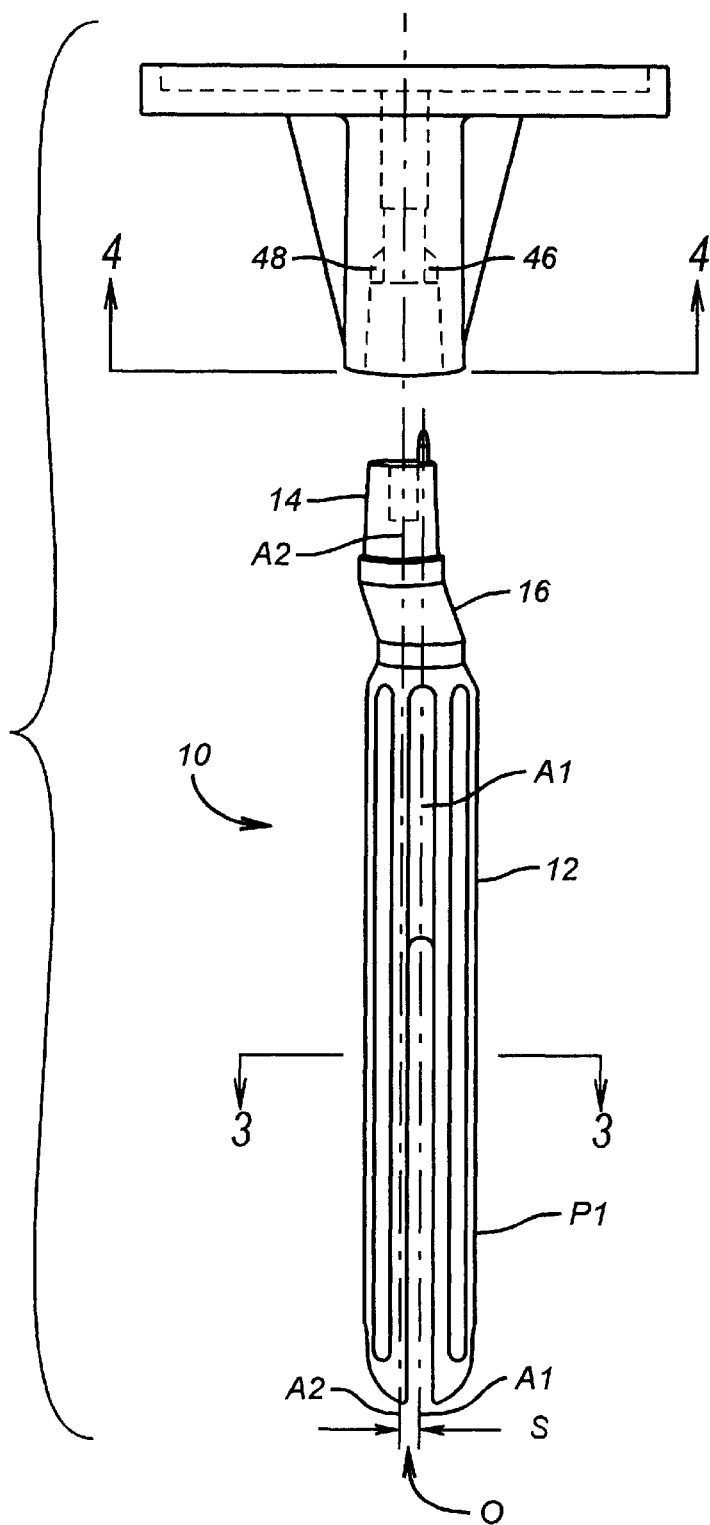
FIG. 1 is a frontal elevation illustrating an embodiment of a stem and baseplate in a first orientation.

An offset press-fit tibial stem is illustrated in FIG. 1, and is designated 10. Stem 10 includes a main body portion 12 and a baseplate connection portion 14. The baseplate connection portion 14 is offset from and connected to the main body portion 12 by an intermediate transition portion 16 which is angularly disposed relative to portions 12 and 14, and functions to provide and offset, designated O, between the main body portion 12 and the baseplate connection portion 14.

The amount of offset O between main body portion 12 and the baseplate connection portion 14 is illustrated by a space, designated S, between a first centroidal axis designated A1 extending through the main body portion 12, and a second centroidal axis designated A2, substantially parallel to the first centroidal axis A1, and extending through the baseplate connection portion 14. The space S is of a dimension, i.e. about 3 mm, such that both the first centroidal axis A1, and the second centroidal axis A2, each pass through the main body portion 12. This dimension has been formed to provide a suitable offset for most required offsets to correct the tibial baseplate position either medially or laterally.

Figure 2:
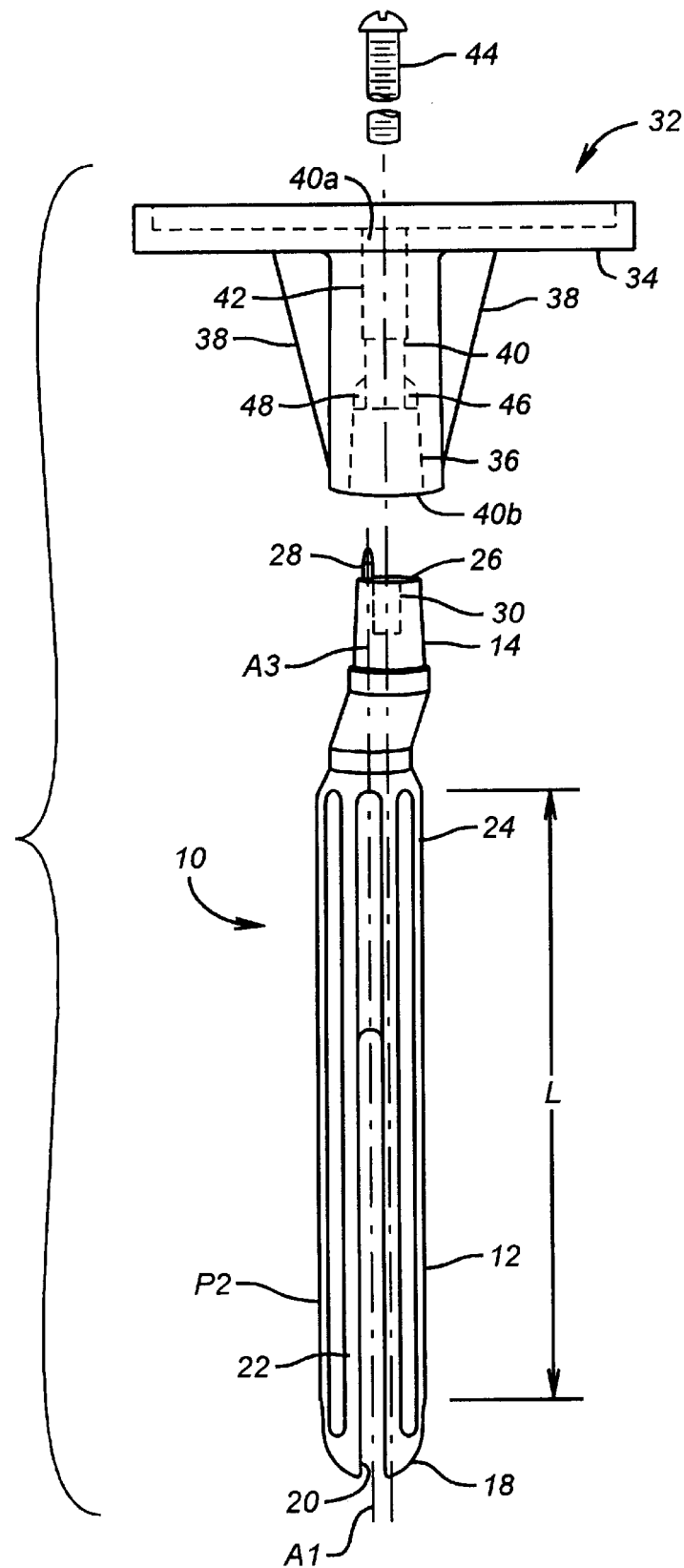
FIG. 2 is a frontal elevation illustrating an embodiment of the stem and baseplate in a second orientation.
Figure 3:
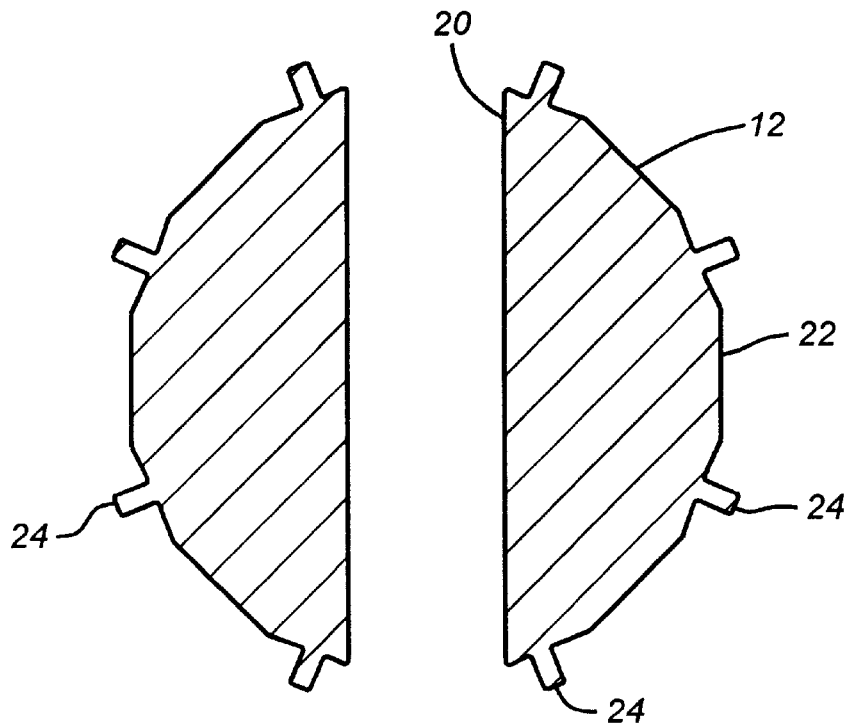
FIG. 3 is a cross-sectional view of the stem taken along line 3—3 of FIG. 1.

Stem 10, FIG. 2, includes an end 18 on the main body portion 12 which includes an elongated slot 20 bifurcating a substantial portion of main body portion 12, and providing some flexibility for radially compressing the first end 18 of main body portion 12, when stem 10 is press-fit into an intermedullary canal. Also, main body portion 12 includes an outer peripheral surface 22, see also FIG. 3, having a plurality of longitudinally extending flutes 24 protruding radially outwardly from surface 22. Flutes 24 are substantially parallel relative to each other and have a length, designated L, FIG. 2, which extend substantially along the entire length of main body portion 12.

Stem 10 also includes an end 26 on the baseplate connection portion 14 having a key member or tab 28 extending axially therefrom and situated on one side of the baseplate connection portion such that a longitudinal axis, designated A3, of tab 28 extends through main body portion 12 and is substantially coincidental with axis A1. End 26 also includes a threaded receiver 30, discussed below in greater detail.

Figure 4:
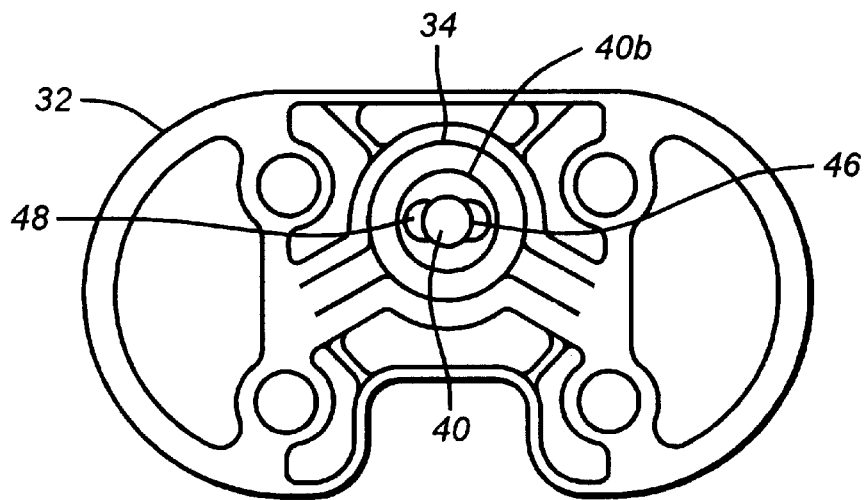
FIG. 4 is an end view of the baseplate taken along the line 4—4 of FIG. 1.

A baseplate 32, FIG. 2, includes a mounting portion 34 and a stem receiver portion 36 attached thereto and reinforced by a pair of flanges 38 extending therebetween. An opening 40 extends entirely through baseplate 32 from mounting portion 34 to stem receiver portion 36. A first end 40a of opening 40 includes an enlarged recess 42 for receiving and recessing a threaded fastener 44 in baseplate 32 when fastener 44 is in threaded contact with threaded receiver 30 in baseplate connection portion 14 of stem 10. A second end 40b of opening 40 includes a pair of keyed slots 46 and 48, see also FIG. 4, which are 180 degrees opposed to each other, for receiving tab 28. Thus tab 28 is inserted into either slot 46 or slot 48 to provide an offset in a first position P1, FIG. 1, e.g. a medial or lateral offset or in a second position, P2, 180 degrees opposite the first position, FIG. 2, e.g. a medial or lateral offset.

Figure 5:
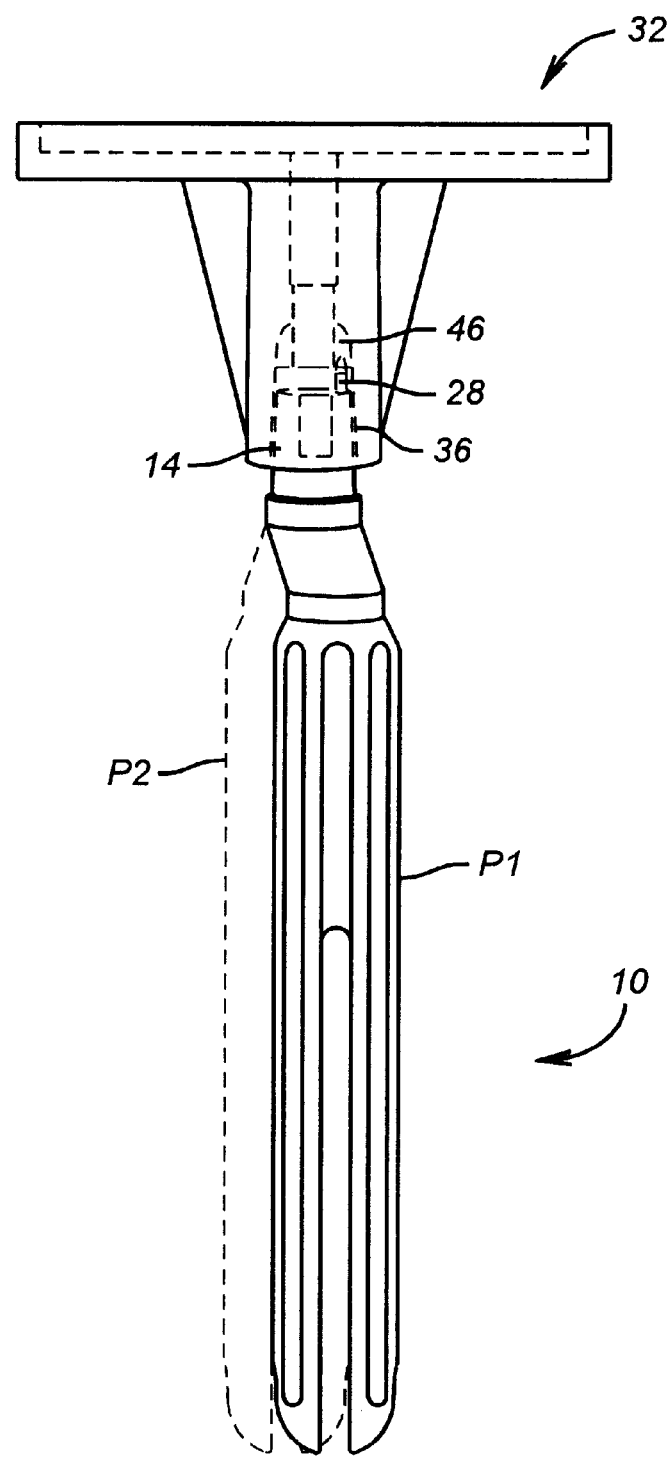
FIG. 5 is a frontal view illustrating an embodiment of the stem in a first orientation attached to the baseplate.

In FIG. 5, stem 10 is illustrated having baseplate connection portion 14 inserted with stem receiver portion 36. Tab 28 extends into slot 46 for a non-rotational connection between stem 10 and baseplate 32 in position P1. Stem 10 can be rotated 180 degrees to position P2, so that tab 28 is non-rotatably engaged with slot 48.

As it can be seen, the principal advantage of this embodiment is that a tibial stem can be press-fit into the intermedullary canal in contact with cortical bone, in a first or a second orientation, and the baseplate can be attached to the stem and centered on the proximal tibial surface without overhang, so as to correct the tibial baseplate position either medially or laterally.

As a result, one embodiment provides an offset, press-fit tibial stem including a main body portion, and a baseplate connection portion which is offset from and connected to the main body portion by a transition portion. The main body portion has a first centroidal axis passing therethrough. The baseplate connection portion has a second centroidal axis passing therethrough. The offset is such that the first and second centroidal axes each pass through the main body portion.

Another embodiment provides an offset, press-fit tibial stem system wherein the stem is attached to a baseplate so that the baseplate can be centered on the proximal tibial surface without overhang to correct the tibial baseplate position either medially or laterally.

A further embodiment provides a method of mounting an offset, press-fit tibial stem system including forming a canal in a tibia by removing cancellous bone. The stem is oriented for either a medial or lateral offset within the canal. The stem includes a baseplate connection portion offset from a main body portion. A baseplate is mounted on the baseplate connection portion of the stem, the offset is such that, a first centroidal axis of the baseplate connection portion, and a second centroidal axis of the main body portion, each pass through the main body portion. The main body portion is press-fit in contact with cortical bone in the canal such that the baseplate is mounted on an end of the tibia, free of overhanging the end of the tibia.

A still further embodiment provides an offset, press-fit tibial stem system including a baseplate having a stem receiving recess formed therein. The recess is keyed for receiving a stem in only one of a first position and a second position. The stem has a main body portion and a baseplate connection portion. The baseplate connection portion is keyed to engage the recess in only one of either the first position or the second position. The baseplate connection portion is offset from, and connected to the main body portion by a transition portion. The main body portion has a first centroidal axis passing therethrough. The baseplate connection portion has a second centroidal axis passing therethrough.

The offset is such that the first and second centroidal axes each pass through the main body portion. In this manner, the first position provides a medial offset between the baseplate and the stem and the second position provides a lateral offset between the baseplate and the stem.

Although illustrative embodiments have been shown and described, a wide range of modifications, change and substitution is contemplated in the foregoing disclosure and in some instances, some features of the embodiments may be employed without a corresponding use of other features. Accordingly, it is appropriate that the appended claims be construed broadly and in a manner consistent with the scope of the embodiments disclosed herein.

What is claimed is:

1. A one-piece offset, press-fit implant stem comprising:

a main body portion;

a baseplate connection portion being offset from and integrally connected to the main body portion;

the main body portion having a first centroidal axis passing therethrough;

the baseplate connection portion having a second centroidal axis passing therethrough; and the offset being such that the first centroidal axis and the second centroidal axis each pass through the main body portion.

2. The stem as defined in claim 1 wherein the baseplate connection portion comprises a first end of the stem and includes a tab adapted to engage a tibial baseplate.

3. The stem as defined in claim 2 wherein the tab projects outwardly from the first end of the stem and orients the stem with the tibial baseplate in either of a first position and a second position.

4. The stem as defined in claim 3 wherein the first position is 180 degrees opposed to the second position.

5. The stem as defined in claim 2 wherein the baseplate connection portion includes a threaded receiver.

6. The stem as defined in claim 2 wherein the main body portion includes a second end, opposite the first end, the second end having an elongated slot bifurcating the second end of the main body portion.

7. The stem as defined in claim 6 wherein the main body portion includes a plurality of longitudinally extending flutes protruding radially from an outer surface thereof.

8. The stem as defined in claim 1 wherein the first axis is substantially parallel to the second axis.

9. The stem as defined in claim 8 wherein the first axis is spaced apart from the second axis by an amount corresponding to the offset.

10. A two-piece offset, press-fit implant stem system comprising:
    a baseplate defining a first piece;
    a stem defining a second piece and having a main body portion and a baseplate connection portion, the baseplate connection portion being attached to the baseplate, and being offset from and integrally connected to the main body portion;
    the main body portion having a first centroidal axis passing therethrough;
    the baseplate connection portion having a second centroidal axis passing therethrough; and
    the offset being such that the second centroidal axis also passes through the main body portion.

11. The system as defined in claim 10 wherein the baseplate includes a first keyed slot and a second keyed slot formed therein, the first keyed slot being 180 degrees opposed to the second keyed slot.

12. The system as defined in claim 11 wherein the baseplate connection portion comprises a first end of the stem and includes a key member in keyed engagement with the baseplate.

13. The system as defined in claim 12 wherein the key member orients the stem with the baseplate in either of a first position and a second position.

14. The system as defined in claim 13 wherein the first position includes the key member in the first keyed slot and the second position includes the key member in the second keyed slot.

15. The system as defined in claim 12 wherein the baseplate connection portion includes a threaded receiver and the baseplate includes a bore formed therethrough which aligns with the threaded receiver.

16. The stem as defined in claim 12 wherein the main body portion includes a second end, opposite the first end, the second end having an elongated slot bifurcating the second end of the main body portion.

17. The stem as defined in claim 16 wherein the main body portion includes a plurality of longitudinally extending flutes protruding radially from an outer surface thereof.

18. The stem as defined in claim 10 wherein the first axis is substantially parallel to the second axis.

19. The stem as defined in claim 18 wherein the first axis is spaced apart from the second axis by an amount corresponding to the offset.

20. A method of mounting a two-piece offset, press-fit tibial stem system comprising the steps of:
    forming a canal in a tibia by removing cancellous bone;
    orienting a stem for one of a medial and a lateral offset within the canal, the stem defining a first piece and having a baseplate connection portion offset from and integrally connected to a main body portion;
    mounting a baseplate on the baseplate connection portion of the stem, the baseplate defining a second piece and the offset being such that, a first centroidal axis of the baseplate connection portion and a second centroidal axis of the main body portion, each pass through the main body portion; and
    press-fitting the main body portion in contact with cortical bone in the canal such that the baseplate is mounted on an end of the tibia free of overhanging the end of the tibia.

21. A two-piece offset, press-fit implant stem system comprising:
    a baseplate defining a first piece and including a stem receiving recess formed therein, the recess being keyed for receiving a stem in one of a first position and a second position;
    the stem defining a second piece having a main body portion integrally connected to a baseplate connection portion;
    the baseplate connection portion being keyed to engage the recess in one of the first position and the second position;
    means for transitioning the baseplate connection portion to be offset from, and connected to, the main body portion;
    the main body portion having a first centroidal axis passing therethrough;
    the baseplate connection having a second centroidal axis passing therethrough; and
    the offset being such that the first centroidal axis and the second centroidal axis each pass through the main body portion, whereby the first position provides a medial offset between the baseplate and the stem and the second position provides a lateral offset between the baseplate and the stem.

22. The system as defined in claim 21 wherein the baseplate connection portion includes an axially extending tab having a third centroidal axis which passes through the main body portion.

23. The system as defined in claim 22 wherein the third centroidal axis is substantially coincident with the first centroidal axis.

24. An offset, press-fit implant stem comprising;
    a main body portion;
    a baseplate connection portion being offset from and connected to the main body portion and having an end with a key member adapted to engage a tibial baseplate wherein the key member orients the stem with the baseplate in either a first position or a second position that is 180 degrees opposed to the first position;
    the main body portion having a first centroidal axis passing therethrough;
    the baseplate connection portion having a second centroidal axis passing therethrough; and
    the offset being such that the first centroidal axis and the second centroidal axis each pass through the main body portion.

25. An offset, press-fit implant stem system comprising:

a baseplate having first and second keyed slots, the first keyed slot being 180 degrees opposed to the second keyed slot;

a stem having a main body portion and a baseplate connection portion, the baseplate connection portion being attached to the baseplate, and being offset from, and connected to, the main body portion by a transition portion;

the main body portion having a first centroidal axis passing therethrough;

the baseplate connection portion having a second centroidal axis passing therethrough; and the offset being such that the second centroidal axis also passes through the main body portion.

26. The system as defined in claim 25 wherein the baseplate connection portion comprises a first end of the stem and includes a key member in keyed engagement with the baseplate.

27. The system as defined in claim 26 wherein the key member orients the stem with the baseplate in either of a first position and a second position.

28. The system as defined in claim 27 wherein the first position includes the key member in the first keyed slot and the second position includes the key member in the second keyed slot.

29. The system as defined in claim 26 wherein the baseplate connection portion includes a threaded receiver and the baseplate includes a bore formed therethrough which aligns with the threaded receiver.

30. The stem as defined in claim 26 wherein the main body portion includes a second end, opposite the first end, the second end having an elongated slot bifurcating the second end of the main body portion.

31. The stem as defined in claim 30 wherein the main body portion includes a plurality of longitudinally extending flutes protruding radially from an outer surface thereof.

\* \* \* \* \*